US006129697A

United States Patent [19]
Drasler et al.

[11] Patent Number: 6,129,697

[45] **Date of Patent: *Oct. 10, 2000**

[54] THROMBECTOMY AND TISSUE REMOVAL DEVICE

[75] Inventors: William J. Drasler, Minnetonka; Robert G. Dutcher, Maple Grove; Mark L. Jenson, Greenfield; Joseph M. Thielen, Buffalo; Emmanuil I. Protonotarios, Brooklyn Park, all of Minn.

[73] Assignee: Possis Medical, Inc., Minneapolis, Minn.

[ * ] Notice: This patent is subject to a terminal disclaimer.

[21] Appl. No.: 08/351,610

[22] Filed: Dec. 8, 1994

Related U.S. Application Data

[60] Division of application No. 07/976,367, Nov. 13, 1992, abandoned, which is a continuation-in-part of application No. 07/563,313, Aug. 6, 1990, abandoned.

[51] Int. Cl.[7] .......... A61B 17/20

[52] U.S. Cl. .......... 604/22; 604/43; 606/159

[58] Field of Search .......... 604/22, 27, 30, 604/35, 41, 43–45, 48, 97, 118, 119, 132, 140, 141, 151, 152, 173, 268, 269; 128/DIG. 12; 606/159, 167

[56] References Cited

U.S. PATENT DOCUMENTS

| | | | |
|---|---|---|---|
| 1,902,418 | 3/1933 | Pilgrim . | |
| 4,690,672 | 9/1987 | Veltrup | 604/43 |
| 4,790,813 | 12/1988 | Kensey | 604/22 |
| 4,898,574 | 2/1990 | Uchiyama et al. | 604/22 |
| 4,913,698 | 4/1990 | Ito et al. | 604/22 |
| 5,135,482 | 8/1992 | Neracher | 604/22 |
| 5,318,518 | 6/1994 | Plechinger et al. | 604/43 |

*Primary Examiner*—Corrine McDermott
*Attorney, Agent, or Firm*—Hugh D. Jaeger

[57] ABSTRACT

A device for removing a thrombus or other tissue deposit from the cardiovascular system, or from a natural or synthetic tubule or cavity found in the human body of a patient without the need to surgically access the location of the thrombus or other tissue deposit via a cut-down or other surgical procedure. A flexible metal or high pressure plastic tube conveys an extremely high pressure stream of sterile saline or other physiologic solution to at least one orifice at the distal end of the catheter. At least one jet is directed at the opening of a large exhaust lumen or other target. The jet is responsible for providing a localized negative pressure which entrains tissue into the jet from break-up of the debris. This jet can also provide stagnation pressure in the exhaust lumen which drives the tissue or thrombotic debris out of the exhaust lumen. Operation of the device with tip pressure greater than 500 psi provides this device with the entrainment and exhaust characteristics which contribute to its effectiveness. The rate of exhaust of tissue debris is metered to ensure minimal local impact on the vasculature at the site of the thrombus deposit. A fluid metering means, such as a roller pump, controls the rate of exhaust such that it is in balance with the saline input or can be adjusted to be greater or less than the input. A positive displacement pump operating at steady or pulsatile flow provides the high pressure saline to the distal end of the catheter.

23 Claims, 9 Drawing Sheets

THROMBECTOMY AND TISSUE REMOVAL DEVICE

CROSS REFERENCE TO CO-PENDING APPLICATIONS

This application is a division, of application Ser. No. 07/976,367, flied Nov. 13, 1992 now abandoned.

This patent application is a continuation-in-part of Ser. No. 07/563,313, filed Aug. 6, 1990, entitled "Thrombectomy Method and Device", assigned to the same assignee as the present patent application, now abandoned.

BACKGROUND OF THE INVENTION

1. Field of the Invention

The present invention relates generally to medical devices and procedures, and more particularly, relates to medical devices and procedures for removing thrombus or other tissue deposits from the cardiovascular system, or from a natural or synthetic tubule or other cavity found in the human body.

2. Description of the Prior Art

Procedures and apparatus have been developed for ease in removing various tissue. U.S. Pat. No. 4,790,813 issued to Kensey and U.S. Pat. No. 4,842,579 issued to Shiber describe techniques for the removal of plaque deposited in arteries by mechanical ablation using rotating cutting surfaces. These relatively traumatic approaches are directed to the treatment and removal of very hard substances.

In current medical procedures, thrombus and other tissue are often removed using a catheter such as is described in U.S. Pat. No. 4,328,811 issued to Fogarty. In this system, a surgical cutdown is performed to access the vessel and allow catheter entry and advancement to a point beyond the deposit. The balloon is inflated and the catheter is withdrawn pulling the tissue along with it.

Pressurized fluids have also been used in the past to flush undesirable substances from body cavities. U.S. Pat. No. 1,902,418 describes such a system for domesticated animals. The more modern approaches tend to use vacuum rather than gravity as the primary means for removal of the deposits or tissue and relatively low fluid pressures to cut into and fragment the substances to be removed.

U.S. Pat. No. 3,930,505 issued to Wallach describes a surgical apparatus for the removal of tissue from the eye of a patient. As with similar systems, Wallach uses a relatively low pressure jet of water (i.e. 15 to 3500 psi) to disintegrate the tissue, and a suction pump to perform the actual removal.

A similar approach applied to the cardiovascular system is discussed in U.S. Pat. No. 4,690,672 issued to Veltrup. Veltrup also provides a much lower pressure jet of water (i.e. less than 450 psi) to fragment deposits. As with Wallach, Veltrup uses a vacuum pump for evacuation of the fragments. The distal end of the Veltrup catheter is repositionable and requires manual entrapment of the deposits, or else the catheter jet must be moved into contact with the deposit in order to accomplish tissue fragmentation. The vacuum applied by the suction duct holds the tissue at its opening while a jet of water breaks up a solid structure at its mouth. This device is basically a suction tube which requires a vacuum to operate, but contains a distal jet aimed at the distal opening in order to reduce blockage of the opening.

SUMMARY OF THE INVENTION

The present invention achieves the removal of unwanted thrombus or tissue by utilizing one or more high-pressure fluid jet(s) at the distal end of a catheter to draw the thrombus or tissue towards the catheter and cut or emulsify the thrombus or tissue; the resulting slurry of thrombus or tissue and fluid can then be removed through an exhaust lumen of the catheter, and the fluid jet(s) can provide energy to drive this exhaust. The present invention overcomes the disadvantages of the prior art systems by operating at higher pressures than those envisioned by Veltrup, thereby providing for entrainment of the thrombus or tissue into the fluid jet(s). In addition, the higher pressures produce a force which can be used to drive the fragmented thrombus or tissue out of the catheter without using vacuum. The catheter can draw nearby thrombus or tissue towards the fluid jet(s), which then fragments it without requiring that the catheter be moved into direct contact or juxtaposition with the thrombus or tissue. The high energy of the jet(s) impinging on the opening to the evacuation lumen eliminates the need for a vacuum pump, as the fragmented debris is removed by the evacuation lumen as it is driven out with a driving force above atmospheric pressure.

According to the present invention, energy is added to the system via an extremely high pressure stream(s) of liquid, solution, suspension, or other fluid, such as saline solution, which is delivered to the distal end of the catheter via a high pressure tubing, which directs jet(s) of high velocity fluid at the opening of an exhaust lumen. This stream(s) serves to dislodge thrombus or tissue deposits, entrain them into the jet(s), emulsify them, and drive them out of an exhaust lumen. Tissue or debris such as thrombus particles are attracted to the jet(s) due to the localized high velocity and resultant localized low pressure. Recirculation patterns and fluid entrainment bring the thrombus or tissue continually into close proximity of the jet(s). Once emulsified by the jet(s), the thrombus or tissue can be removed through the exhaust lumen by flow generated as a result of stagnation pressure which is induced at the mouth of the exhaust lumen by conversion of kinetic energy to potential energy (i.e., pressure) of at least one fluid jet directed at and impinging on the lumen mouth. The pressure in the high pressure fluid tubing must be great enough to generate a high localized velocity and, hence, a low localized pressure necessary to entrain the surrounding thrombus or tissue. A high enough pressure to generate substantial stagnation pressure at the opening to the exhaust lumen is necessary to drive the exhaust flow. A pressure of at least 500 psi is needed for the high pressure fluid at the distal end, and pressures of over 1000 psi will provide even better entrainment and stagnation pressures. The stagnation pressure formed at the mouth of the exhaust lumen serves to drive the fragmented thrombus or tissue out of the exhaust lumen. This pressure can typically be greater than one atmosphere and, therefore, provides a greater driving force for exhaust than can be accomplished by using a vacuum pump. Additional jets of lower energy may be directed radially outwardly to aid in removal of thrombus or tissue from the vessel wall and provide a recirculation pattern which can bring fragmented thrombus or tissue into contact with the jet(s) impinging on the exhaust lumen opening.

The procedure is practiced by percutaneously or intraoperatively entering the vascular system, tubule, or other body cavity of the patient at a convenient location with a cannula. The catheter may be inserted either directly or over a previously positioned guidewire and advanced under fluoroscopy, angioscopy or ultrasound device to the site of the vascular occlusion, obstruction or tissue deposit. The exhaust lumen can permit the passage of an angioplasty dilation catheter, guidewire, angioscope, or intravascular ultrasound catheter for intravascular viewing. The lesion site may contain an aggregation of blood factors and cells, thrombus deposit, or other tissues which are normally identified by angiography or other diagnostic procedure. One or more balloons may be inflated to stabilize the distal end of the catheter and provide a degree of isolation of the area to be treated. An isolation balloon located proximal to the high pressure fluid jet(s) can prohibit fragmented tissues from migrating proximally around the outside of the catheter shaft and immobilizing into a side branch of a blood vessel. An isolation balloon distal to the high pressure fluid jet(s) can prohibit embolization distally. This may be of greater importance if embolization of fragmented debris may generate unfavorable clinical sequelae. Thrombolytic drugs such as streptokinase, urokinase, or tPA, and other drugs may be delivered through the catheter along with the saline (or other fluid) or separately to adjunctively aid in the treatment of the lesion. A balloon may also be located at the distal end of the catheter to provide the capability of dilation of the vessel, tubule, or cavity either prior to or following the thrombus or tissue ablation and removal.

The catheter described herein is a part of a device in the first embodiment (FIG. 1) which includes a high pressure fluid supply, the fluid being either sterile saline or other suitable physiological solution compatible with the site of catheter operation within the body. The high pressure of the fluid can be generated with a positive displacement pump, such as a piston pump, which can be made to operate with either pulsatile flow or with steady flow. The catheter and the piston pump can be sterile. A nonsterile motor and motor control system can be used to power the piston pump. Sterile saline and physiological solution available to radiological, cardiological and operative sites can be used as a source of fluid from the high pressure positive displacement pump. The high pressure fluid flow from the pump is supplied via a high pressure tube to the distal end of the catheter where at least one jet of fluid is directed toward the opening of an exhaust lumen. A metering device may also be a part of the device which includes the catheter and the high pressure fluid supply. A metering system can be utilized at the proximal end of the exhaust lumen to regulate the flow rate of the fragmented thrombus or tissue out of the catheter. The flow of fragmented thrombus or tissue out of the exhaust lumen can exceed the flow of high pressure fluid from the jet(s) which impinge on its distal opening. As a result, a metering device can be used to reduce the volumetric outflow rate of fragmented thrombus or tissue such that it is equal to, or in balance with, the volumetric rate of high pressure fluid being supplied to the distal end. This balance of flow would then ensure that the fluid volume within a blood vessel, tubule or body cavity is not being significantly altered during the thrombectomy or tissue removal procedure. The outlet flow rate of the thrombus or tissue fragments can also be adjusted such that it is either greater than or less than the high pressure fluid supply rate, in order to either drain or expand the fluid volume within the vessel or cavity. The metering device can be any device with means of measuring the outlet flow rate and adjusting it to a desired magnitude. A roller (peristaltic) pump can be used as a metering device in this application. When used with a specific tubing and rotational speed, prescribed volumetric output of the fragmented thrombus or tissue will be exhausted.

A manifold attaches to the proximal end of the catheter to provide leak-free access pathways for the high pressure fluid supply, the exhaust pathway for fragmented thrombus or tissue to be delivered to a collection reservoir, the pathway for fluid (either gas or liquid) for inflation of balloon(s) at the distal end of the catheter (if desired), and the access port for introducing an auxiliary diagnostic or therapeutic device available to the physician. Such therapeutic devices may include a guidewire used to guide the catheter to its appropriate site in a vessel, tubule or cavity. A diagnostic device may include an ultrasound catheter or an angioscope. Contrast agents, thrombolytic drugs, or other drugs may also be delivered to the lesion site either using the exhaust lumen or the high pressure supply tube. A balloon inflation means can be connected to the manifold to deliver a gas or fluid to inflate a balloon(s) located at the distal end of the catheter. Such balloon(s) can serve either to reduce embolization of fragmented thrombus or tissue or to dilate the lesion. The balloon inflation means can be a sterile syringe or other device available for inflation of angioplasty catheter balloons.

According to the second embodiment of the present invention (FIG. 3), there is provided a thrombectomy or tissue removal catheter having a manifold at the proximal end and having a distal end which enters percutaneously into a blood vessel, tubule, or cavity of the body in order to fragment thrombus or other tissue obstruction and remove the fragments out of the body. The saline or other high pressure fluid enters the catheter manifold and is routed via a high pressure conduit such as a hypo tube or polyimide tube to the distal end of the catheter where it exits through at least one orifice, which forms one or more jet(s) of high pressure fluid which are directed at the opening of an exhaust lumen. The exhaust lumen carries the fragmented thrombus or tissue from the distal end of the catheter to the manifold which is located outside the body. The high pressure tubing forms a loop at the distal end with the plane of the loop being perpendicular to the axis of the catheter shaft. Holes drilled into the loop form the orifices which direct jets of fluid in a proximal direction back towards the opening of the exhaust lumen. One or more of these jets provides the stagnation pressure at the opening of the exhaust lumen to drive a volumetric outflow of fragmented thrombus or tissue, which can be greater than the flow rate of the high pressure fluid. The stagnation pressure can be higher than one atmosphere, thereby generating a greater exhaust rate than can be accomplished by creating a vacuum at the proximal end of the exhaust lumen with a vacuum pump. The development of a stagnation pressure at the opening of the exhaust lumen requires a pressure within the high pressure tubing at the distal end to be at least 500 psi with improved results occurring with pressures of over 1000 psi. In order to obtain significant entrainment of thrombus or tissue into the high velocity jet(s) as a result of their localized low pressure, it is necessary to operate the device with the pressure of the fluid in the high pressure tubing at the distal end being at least 500 psi. Without high pressure, the amount of entrainment of surrounding tissue or thrombus, which moves into the jet for ablation, is minimal, and the catheter would require direct contact of the jet(s) or juxtaposition with the material to be fragmented. A distal pressure of over 1000 psi for the high pressure fluid provides improved entrainment of thrombus or tissue into the jet(s) for fragmentation. The formation of a loop in the distal portion of the high pressure tubing provides the catheter with the capability of following over a standard guidewire (which then would be located within the loop) while still maintaining unobstructed access to the thrombus or tissue entrained in a jet, as well as access for at least one jet unobstructed by the guidewire to impinge on the exhaust lumen and generate the stagnation pressure to drive thrombus or tissue fragment exhaust. The guidewire can follow through the exhaust lumen of the catheter to efficiently utilize the available space and minimize the diameter of the catheter shaft. The distance between the orifice(s) and the entrance to the exhaust lumen is another important variable in determining the amount of stagnation pressure generated. A distance of one to five millimeters will provide adequate stagnation pressure to drive exhaust, and still provide enough space for thrombus or tissue to become entrained for fragmentation. As this distance becomes greater, there is a tendency towards significantly less stagnation pressure; as the distance becomes smaller, little or no benefit is gained due to limited entrainment.

In the third embodiment of the invention (FIG. 8), there is provided a thrombus or tissue removal catheter similar in every way to that of the second embodiment except that the orifice(s) are located a further distance away from the opening to the exhaust lumen. At a distance of greater than five millimeters, the jet spray pattern tends to fan out with much of the spray missing the exhaust lumen and also a great loss in its kinetic energy. Even though this device does not generate enough stagnation pressure to drive the exhaust flow, it still will be fully capable of entraining thrombus or tissue into the jet as long as the pressure within the high pressure tubing at the distal end is greater than 500 psi. The catheter, therefore, does not have to be brought into juxtaposition or contact with thrombus or tissue for it to fragment the thrombus or tissue. The localized negative pressure will draw the thrombus or tissue into the jet(s). Exhaust can be accomplished in this case by applying a vacuum or suction as needed.

According to the fourth embodiment of the invention (FIG. 9), there is provided a catheter similar to that of the second embodiment except with the addition of the following feature which can add to its performance. This device provides additional radially directed jet(s) of fluid to the distal end of the catheter. These additional jet(s) are directed with radial component outwards in order to help dislodge the thrombus or tissues from the blood vessel, tubule, or cavity. The outward jet(s) are of a lower velocity than the jet(s) which direct fluid at the opening of the exhaust lumen. The lower velocity jet(s) will not damage the vessel wall or cause damage to the blood which they may contact. Approximately three jets will clean the perimeter of a vessel or tubule, and will set up a recirculation pattern where the fluid from the radial jet(s) is directed to form a path leading toward the localized low pressure region of the high velocity jets directed at the opening of the exhaust lumen. This recirculation pattern helps to clean the vessel or tubule with greater efficiency.

According to the fifth embodiment of the invention (FIG. 14), there is provided a catheter similar to that of the first or fourth embodiment except that the following additional features have been added to help performance in specific applications. The catheter shaft tubing can be constructed of plastic with a dual lumen which can provide one lumen for exhaust in a manner similar to the second embodiment and a second lumen for carrying a fluid (either gas or fluid) for inflation of a balloon located on the distal end of the catheter. The balloon can be constructed of latex, silicone, polyurethane, or other elastic material and can serve to center the catheter, as well as isolate the distal end of the catheter so that fragments cannot migrate past the balloon. A balloon of this type could be located either proximal or distal to the fluid jet(s) and exhaust lumen opening or in both locations. A dilation balloon constructed out of polyolefin, polyethylene, polyvinylchloride, polyethylene terephthalate, or other high strength plastic could be similarly located at the distal end of the catheter. Such a balloon could be used to dilate a vessel lesion either before or after the catheter has removed tissue deposits such as thrombus. This catheter contains a separate tubing to carry the high pressure fluid from the manifold to the distal end to supply the high velocity jet(s).

According to the sixth embodiment of the invention (FIG. 16), there is provided a thrombus or tissue fragmentation catheter that does not remove the fragmented thrombus or tissue. The device contains a high pressure fluid tube such as a hypo tube which delivers high pressure fluid to one or more orifices which direct jet(s) of fluid proximally toward the surface. The surface serves as a target for the jet(s), providing an element of safety to the catheter by prohibiting direct impingement of the jet(s) on the wall of a blood vessel, tubule or duct. The jet(s) have high velocity and low localized pressure due to the high fluid pressure of at least 500 psi in the high pressure tube. Therefore, the jet(s) can both entrain thrombus or tissue onto the jet(s), and break up the tissue or thrombus into fragments. No lumen is available in this catheter for exhaust of the fragments. The impingement surface can be made with an opening, which would allow for guidewire passage, although it is not required. The distal end of the hypo tube can be made into a loop to provide for guidewire passage, although it is not required. Fragments generated by this device can be allowed to remain in the vessel, tubule, or cavity, and may embolize with blood flow, or may be washed out using other means.

According to the seventh embodiment of the invention, which applies to previous embodiments that contain an exhaust lumen, there is provided a catheter with a high pressure tube to deliver high pressure fluid from the proximal end of the catheter to the distal end where the fluid is directed by one or more orifices at high velocity onto the distal opening of an exhaust lumen. The pressure in the high pressure tubing at the distal end is at least 500 psi in order to effectively break up the thrombus or tissue deposit. A suction may be applied to the proximal end of the exhaust lumen with a vacuum pump to provide for removal of the fragmented thrombus or tissue, or a roller pump may be used to accomplish a similar effect. The pressure in the high pressure tubing at the distal end may be greater than 500 psi with improved tissue fragmentation occurring at pressures over 1000 psi. Entrainment of tissue such as thrombus into the localized low pressure region of the high velocity jet(s) allows the device to operate effectively without requiring direct contact or juxtaposition of the catheter with neighboring tissue deposit. The distal end of the high pressure tube may form a small arc in order to direct the jet(s) of high pressure fluid proximally toward the opening of the exhaust lumen, or it may form a loop perpendicular to the axis of the catheter shaft in order to direct several jets of fluid rearwards. The loop allows the catheter to follow over a guidewire to reach the lesion site and to effectively fragment thrombus or tissue around the entire perimeter of the guidewire, vessel, tubule, or body cavity.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

Figure 9:
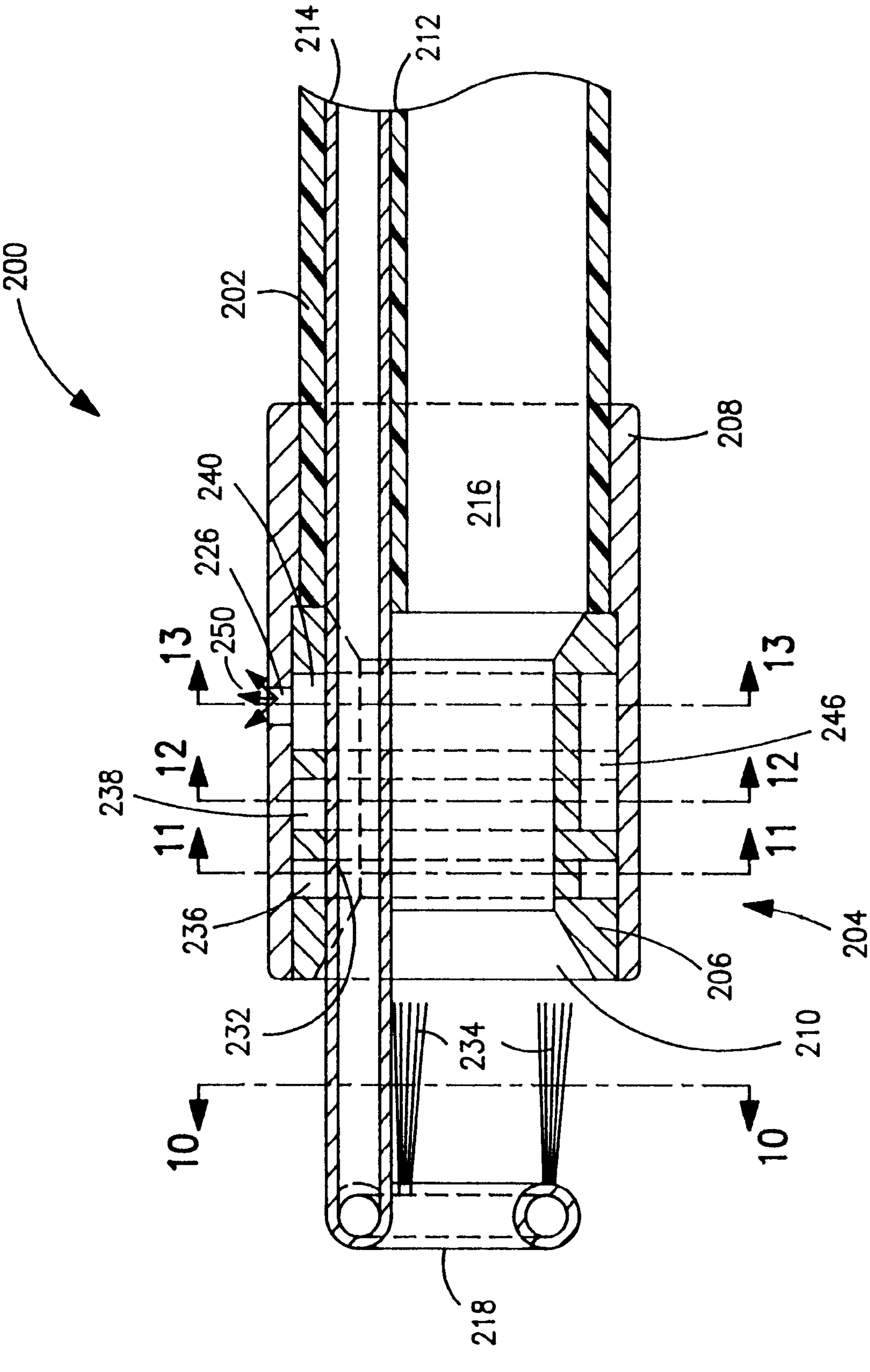
Figure 10:
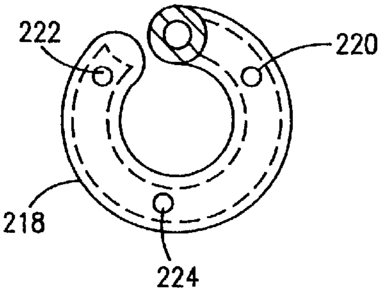
Figure 11:
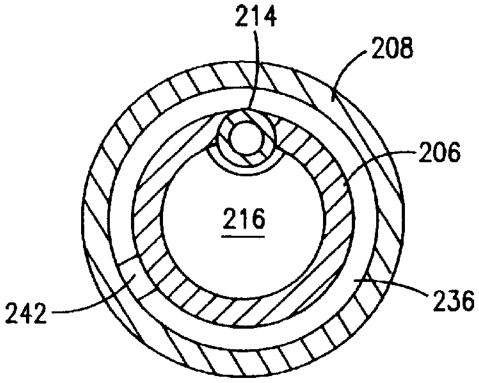
Figure 12:
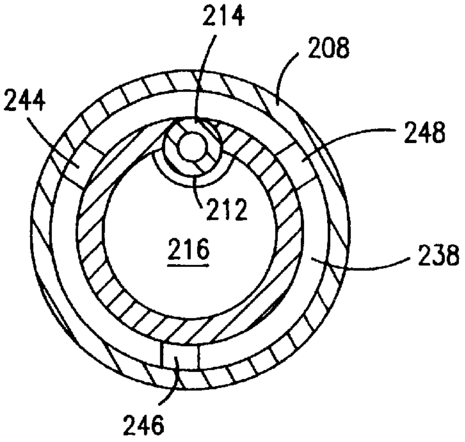
Figure 13:
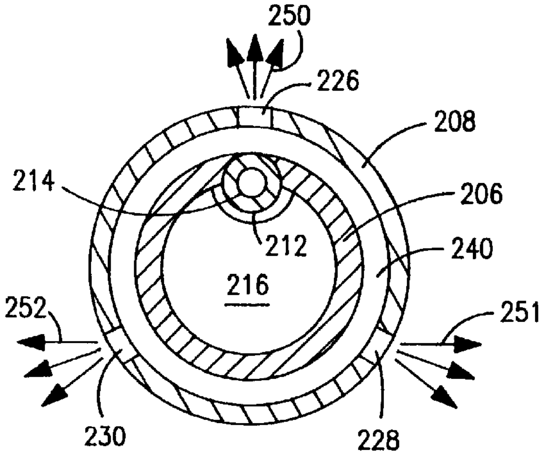
Figure 14:
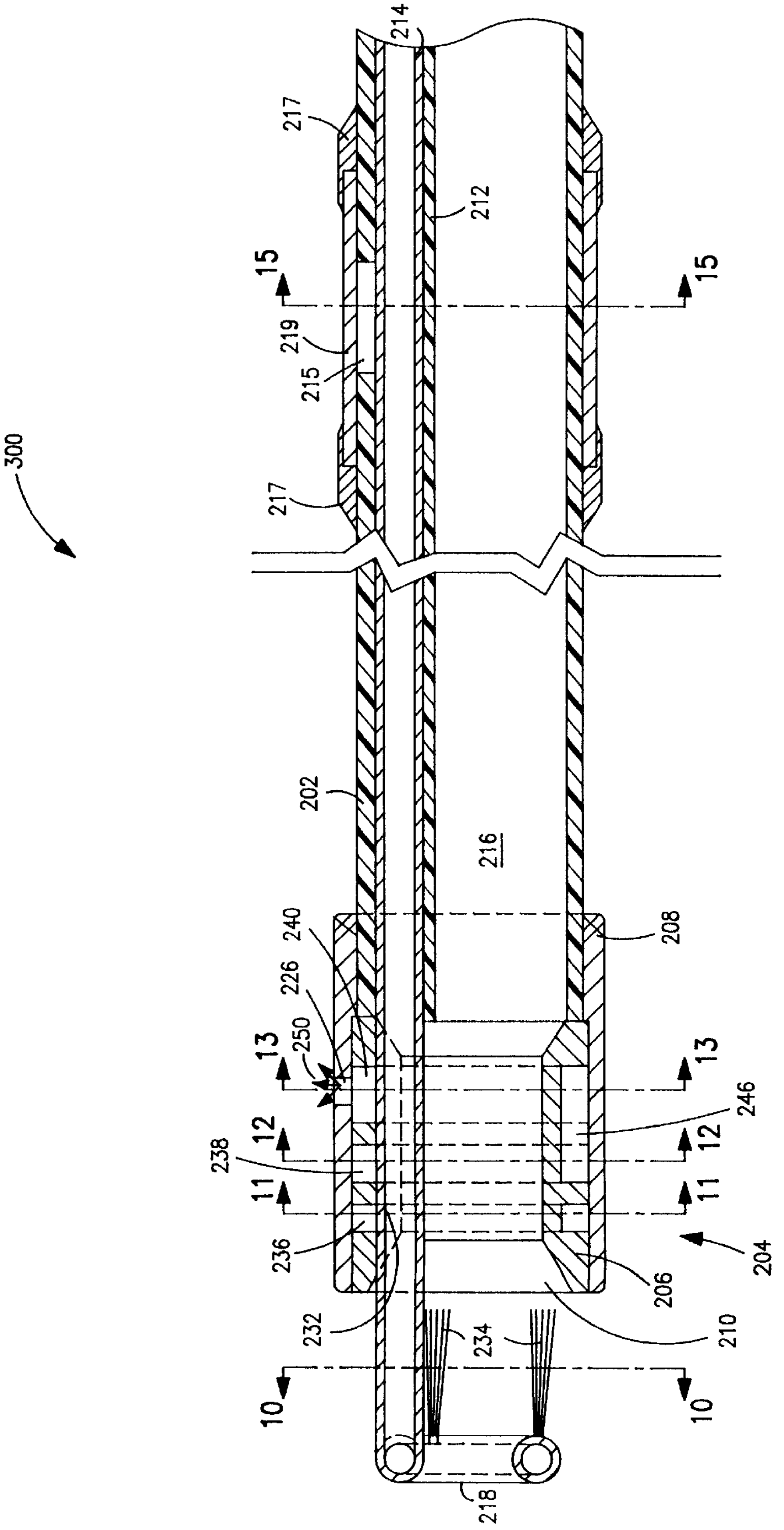
Figure 15:
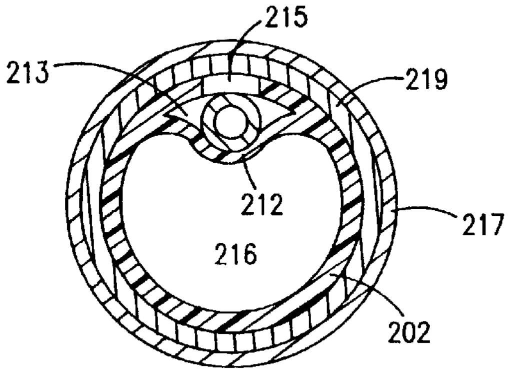
Figure 16:
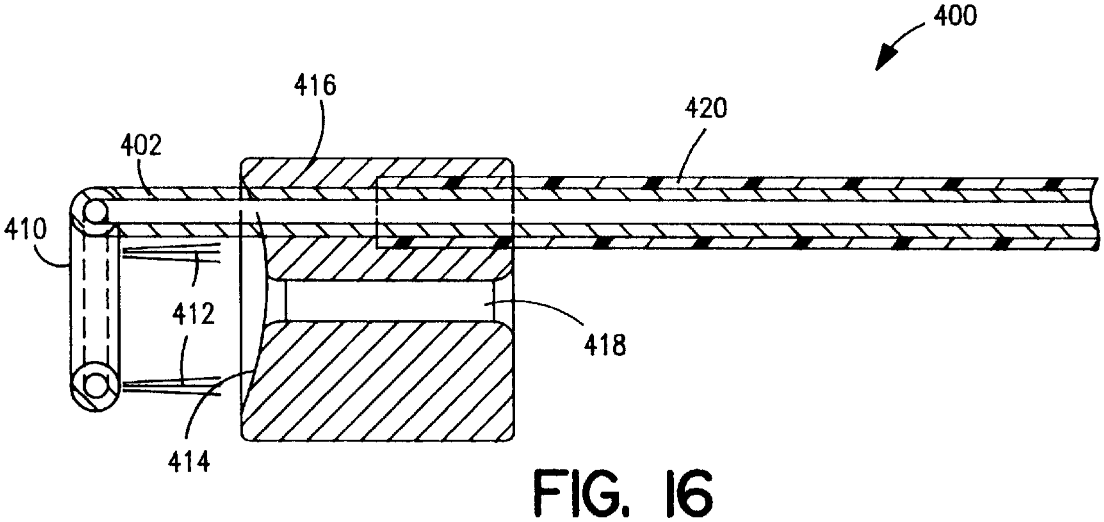
Figure 17:
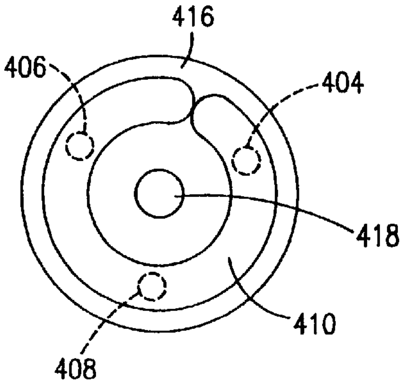

PIG. 9, an alternative embodiment, illustrates a cross-sectional view of another catheter distal end;

FIG. 10 illustrates a cross-sectional view along line 10—10 of FIG. 9 and also FIG. 14;

FIG. 11 illustrates a cross-sectional view along line 11—11 of FIG. 9 and also FIG. 14;

FIG. 12 illustrates a cross-sectional view along line 12—12 of FIG. 9 and also FIG. 14;

FIG. 13 illustrates a cross-sectional view along line 13—13 of FIG. 9 and also FIG. 14;

FIG. 14, an alternative embodiment, illustrates a cross-sectional view of another catheter distal end;

FIG. 15 illustrates a cross-sectional view along line 15—15 of FIG. 14;

FIG. 16, an alternative embodiment, illustrates a cross-sectional view of another catheter distal end; and, FIG. 17 illustrates an end view of the catheter distal end of FIG. 16.

DESCRIPTION OF THE PREFERRED EMBODIMENTS

Figure 1:
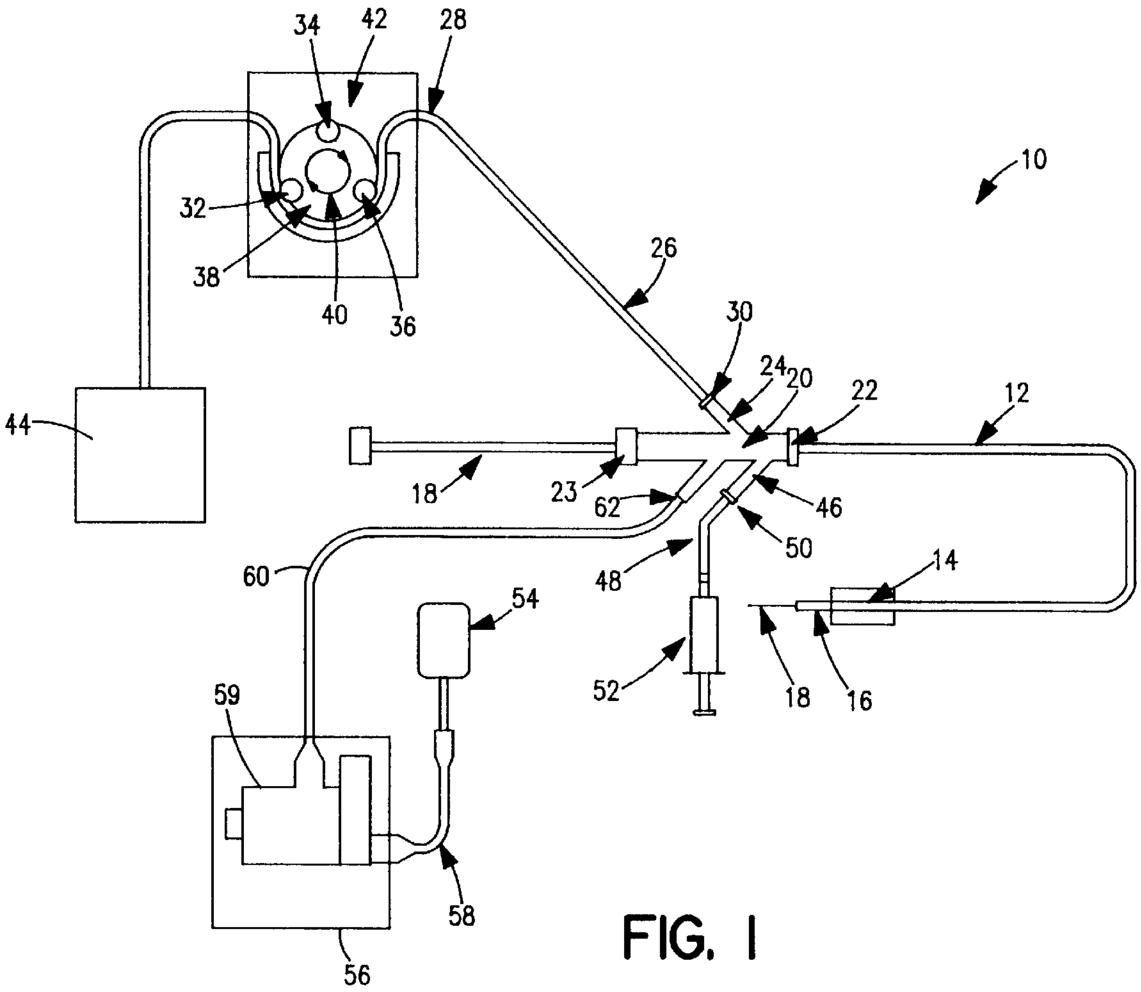
FIG. 1 is a schematic view of one embodiment of the present invention, a thrombectomy and tissue removal device.

FIG. 1 is a schematic view of one embodiment of a thrombectomy and tissue removal device 10 according to the present invention. The details supplied herein should be taken as representative and not limiting of the many embodiments which may be efficaciously employed within the scope of the present invention.

Thrombectomy and tissue removal device 10 has a two-passage tubular member such as a standard two-lumen catheter 12, which is extruded of a flexible material such as polyolefin, PTFE, PVC, polyurethane, nylon, or other suitable material in the normal fashion. Near the distal end 16 of catheter 12 can be located inflatable balloon 14, which is preferably an elastic balloon having no predefined outside diameter size limitation upon inflation. In this manner, balloon 14 can conform to the exact dimensions of the vessel to hold distal end 16 of catheter 12 in a fixed position. Alternatively, inflatable balloon 14 can be an inelastic balloon with a predefined shape and size to permit it to be also used for dilation as in translumenal angioplasty. Distal end 16 of catheter 12 is described in more detail in the figures that follow. Alternatively, the catheter 12 can be made without balloon 14 at all.

Guidewire 18 is optionally available for positioning the catheter 12 as an over-the-wire system; or other diagnostic or therapeutic devices can be used along with the catheter, and may occupy the same lumen as occupied by a guidewire 18. Guidewire 18 passes through the larger of the two lumens of catheter 12 as described in more detail below.

A manifold 20 which is molded of a rigid plastic or other suitable material couples to catheter 12. The main branch of the manifold 20 couples to the larger of the lumens of catheter 12 and has a standard seal assembly 22 applied to the proximal end to sealingly engage the catheter 12. The guidewire 18 sealingly engages manifold 20 by a standard seal assembly 23.

Secondary branch 24 of manifold 20 is also coupled to the larger lumen to provide for evacuation of the emulsified thrombus deposits. Secondary branch 24 sealingly engages distal end 26 of effluent tubing 28 via seal assembly 30.

The flow of effluent through flexible effluent tubing 28 is metered by rollers 32, 34, and 36 as rotated by rotor 38 in the direction of arrows 40 or any other type of controlled metering structure. It must be emphasized that the effluent in flexible tubing 28 is under pressure and, therefore, need not be pumped by roller (peristaltic) pump 42, which merely restricts and meters the flow. This metering could equally well be accomplished with a timed mechanical valve (not shown) which controls the outflow rate. After metering, the effluent from flexible effluent tubing 28 is deposited in tissue fragment collection reservoir 44.

Another secondary branch 46 of manifold 20 is sealingly coupled to inflation tube 48 by seal assembly 50. Inflation and deflation of inflatable balloon 14 is controlled by balloon inflation fluid means 52 in the customary manner.

The solution used to emulsify the thrombus deposit is derived from the standard sterile fluid (e.g., saline) container 54, which may be commercially available. The saline or other solution is transferred to the high pressure supply means 56 via tubing and coupling assembly 58. This is a low pressure fluid path.

The high pressure supply means 56 can be a positive displacement piston pump 59. It is made to be completely disposable for sanitary reasons. The pump 59 can operate under pulsatile or steady flow.

The high pressure output of disposable pump 59 is coupled by a high pressure fluid tube 60 of the catheter by a connection 62 made at another secondary branch 62 of the manifold 20.

Figure 2:
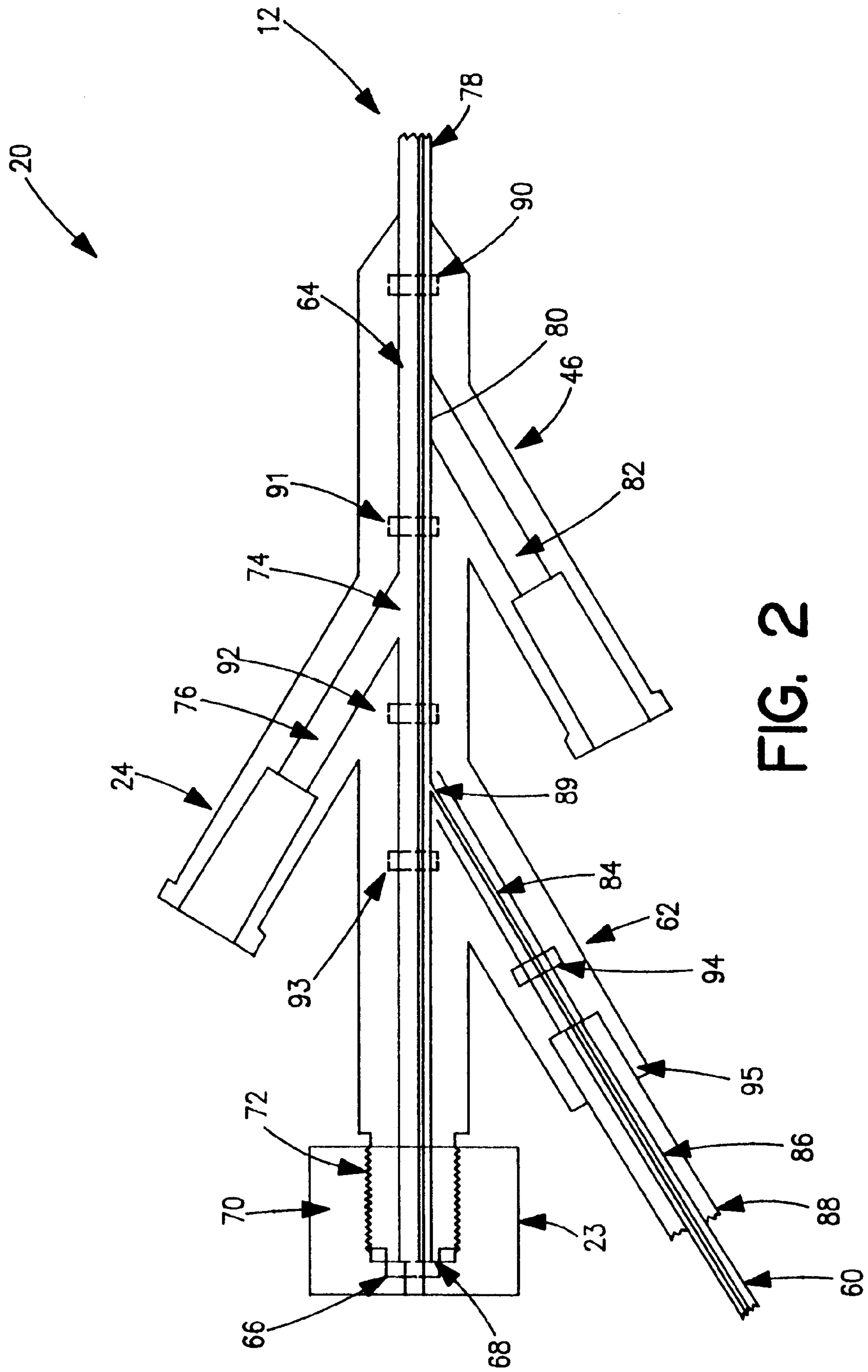
FIG. 2 illustrates a cross-sectional view of a manifold.

FIG. 2 is a cross sectional view of manifold 20 which includes the proximal end of the flexible two-lumen catheter 12. This component can be molded as two halves, which are solvent-bonded together, this view showing one of the two possible halves. As described above, catheter 12 is a two lumen catheter. In the preferred mode, each of the two lumens has two distinct functions. Therefore, manifold 20 serves to provide passage for a high pressure tubing and balloon inflation through one lumen and passage of a guidewire and evacuation through the other lumen.

The larger lumen of catheter 12 is lumen 64. It is used for passage of guidewire 18 (not shown in this view) and for evacuation of effluent and possible passage of a therapeutic angioplasty dilatation catheter, dilatation guidewire, angioscopic probe, or other therapeutic or diagnostic device. Lumen 64 extends through manifold 20 to the proximal end of the manifold and provides passage of a guidewire or other diagnostic or therapeutic device. Guidewire 18 is sealed by compressible circular seal 66 which is compressed by surface 68 as threaded knob 70 is tightened on threads 72. It is important to seal guide wire 18 in this way as guidewire 18 must be movable with respect to catheter 12 to properly manipulate distal end 16 of catheter 12 into position.

Lumen 64 is also terminated at secondary branch 24. This is accomplished by removing a portion of the outer wall of lumen 64 at point 74. This provides fluid coupling between lumen 64 and lumen 76 of secondary branch 24.

The smaller lumen of catheter 12 is lumen 78. One of its functions is as a fluid passageway for the inflation of balloon

14. This function is accomplished by removing a portion of the outer wall of lumen 78 at point 80 to fluid couple lumen 78 to lumen 82 of secondary branch 46.

The remaining purpose of lumen 78 is to provide for passage of metallic tubing 84. Because of the extremely high pressures involved, the saline or other solution is conveyed in a metallic tubing 84, which is preferably stainless steel hypo tubing. To handle the pressures involved, the hypo tubing is run as a continuous length along catheter 12. The proximal end of metallic tubing 84 passes through the outer wall of lumen 78 at point 89 and into secondary branch 62. A larger diameter hypo tube 60 is brazed onto hypo tube 84 at point 86. Alternatively, the larger diameter hypo tube 60 may be attached to hypo tube 84 with a removable connection. This larger tubing 60 is covered by protective plastic tubing 88. Manifold 20 is solvent-bonded together prior to assembly of the catheter, and points 90, 91, 92, 93 and 94 are used to introduce an adhesive which serves as a seal to separate each path and each lumen. Point 95 shows the bonding of the outer plastic tubing 88 which surrounds the high pressure supply tube 60 to the manifold.

Figure 3:
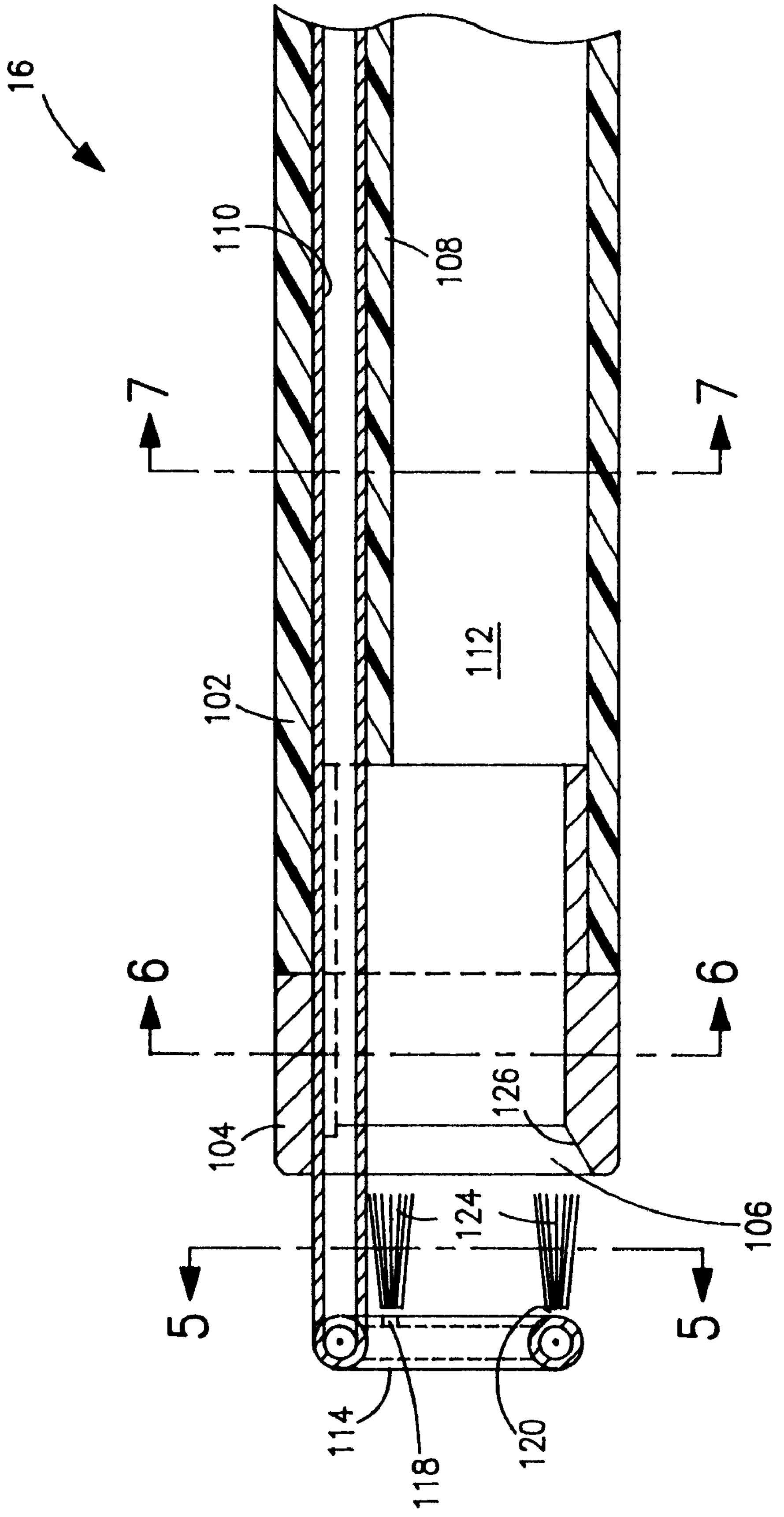
FIG. 3 illustrates a cross-sectional view of a catheter distal end of the present invention.

FIG. 3 illustrates a cross-sectional view of catheter distal end 16 including an outer plastic sheath 102, a tip 104 having a large external orifice 106, a septum 108 encompassing a hypo tube 110 and holding it to the inner surface of the outer plastic sheath 102, and an evacuation lumen 112 incorporating the large external orifice 106 and further formed by the inner surface of the outer plastic sheath 102 and the septum 108. A loop 114 is located at the distal end of the hypo tube 110. The loop 114 allows the catheter to follow easily over a guidewire, but the distal end of the hypo tube is not required to be looped. Orifices 116, 118 and 120 serve to direct saline jets 124 of fluid (e.g., saline) into the external orifice 106 which communicates with the evacuation lumen 112.

The saline fluid jets 124 are directed out of the orifices 116, 118 and 120 in the loop 114 and back toward the external orifice 106 to the evacuation lumen 112. A beveled surface 126 is included on the outer portion of the tip 104 to help direct fluid flow to the evacuation lumen 112. There are no fluid jets shooting in an outward direction. Since some blood vessels and tubules are smaller in diameter, one does not require outward shooting fluid jets. Also, the absence of outward shooting fluid jets makes this design safe with low risk of vessel damage or spasm. The simplicity of the design allows the device to be made with a small diameter at the tip (i.e., 4F or 0.052"). The catheter can be made with diameters ranging from 2F to 10F (0.026"–0.130") or larger if desired. The loop 114 in the hypo tube 110 still allows the device to follow a guidewire without causing damage to the vessel. More than three orifices could be used with some tradeoffs of advantages and disadvantages, but this will not offer much advantage. More orifices of the same size will result in a greater effluent flow rate to be removed due to the additional fluid jets. More orifices of a smaller diameter will result in a greater chance of plugging and a lower penetration distance capability for the jetted fluid in order to maintain the total jet flow rate at an appropriate level. If the total jet flow rate becomes too large, the pressure energy loss in the high pressure tube becomes very large and requires excessive liquid pressure at the proximal end of the high pressure tube. Two fluid jets could be used instead of three, but the ability of the catheter to clean around the entire vessel perimeter becomes hampered. A single fluid jet does not work well when a guidewire is in place since the guidewire blocks entry of thrombus. Also, a loop is very helpful to allow the catheter to track closely over a guidewire without inducing trauma to the vessel.

This catheter when operated with a distal pressure in the high pressure lumen of at least 500 psi will entrain thrombus or tissue deposit into the one or more proximally shooting fluid jet(s) 124 before it reaches the external orifice 106 to the evacuation lumen 112. If the distance from the orifice(s) to the external orifice 106 of the evacuation lumen is relatively close, such as 1–5 mm with an average distance of approximately 3 mm, the fluid jet(s) will generate a stagnation pressure at the orifices which can exceed 1 atmosphere, and will drive the evacuation of the fragmented tissue out of the evacuation lumen 112 without the need for a vacuum pump or any application of suction. Instead, a metering means, such as that of FIG. 1, can be applied. to the proximal end of the evacuation lumen 112 to control the rate of evacuation as desired. The roller (peristaltic) pump 42 of FIG. 1 can serve as this metering means to control the rate of evacuation such that it is greater than, equal to, or less than the flow rate of fluid exiting the orifices at the distal end of the high pressure tube 110.

Figure 4:
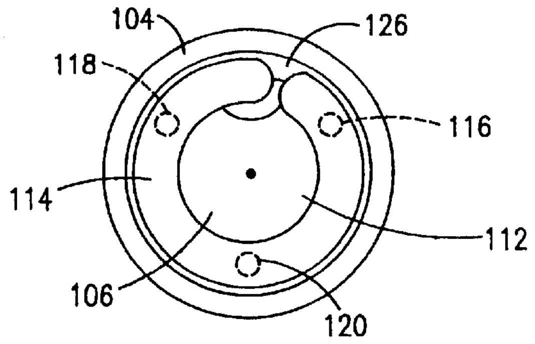
FIG. 4 illustrates an end view of the loop of FIG. 3.

FIG. 4 illustrates an end view of the loop 114 where all numerals correspond to those elements previously described.

Figure 5:
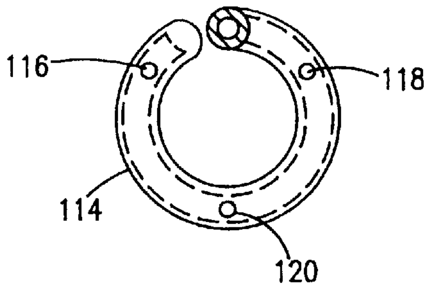
FIG. 5 illustrates a cross-sectional view along line 5—5 of FIG. 3.

FIG. 5 illustrates a cross-sectional view along line 5—5 of FIG. 3 illustrating the orifices 116, 118 and 120 where all other numerals correspond to those elements previously described.

Figure 6:
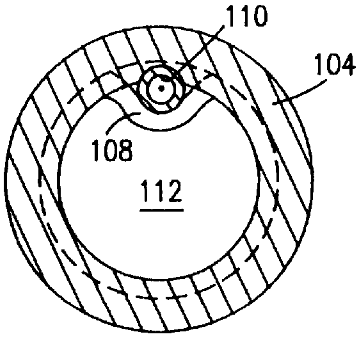
FIG. 6 illustrates a cross-sectional view along line 6—6 of FIG. 3.

FIG. 6 illustrates a cross-sectional view along line 6—6 of FIG. 3 illustrating the exhaust lumen 112 in the area of the tip 104. All other numerals correspond to those elements previously described.

Figure 7:
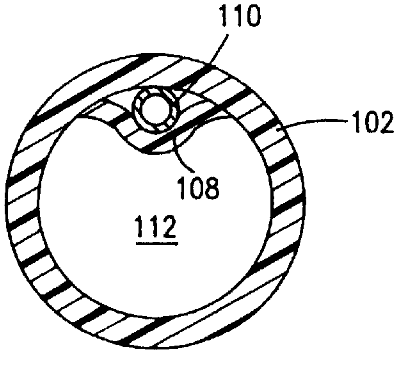
FIG. 7 illustrates a cross-sectional view along line 7—7 of FIG. 3.

FIG. 7 illustrates a cross-sectional view along line 7—7 of FIG. 3 illustrating the exhaust lumen 112 in the distal area of the catheter 12. All other numerals correspond to those elements previously described.

Figure 8:
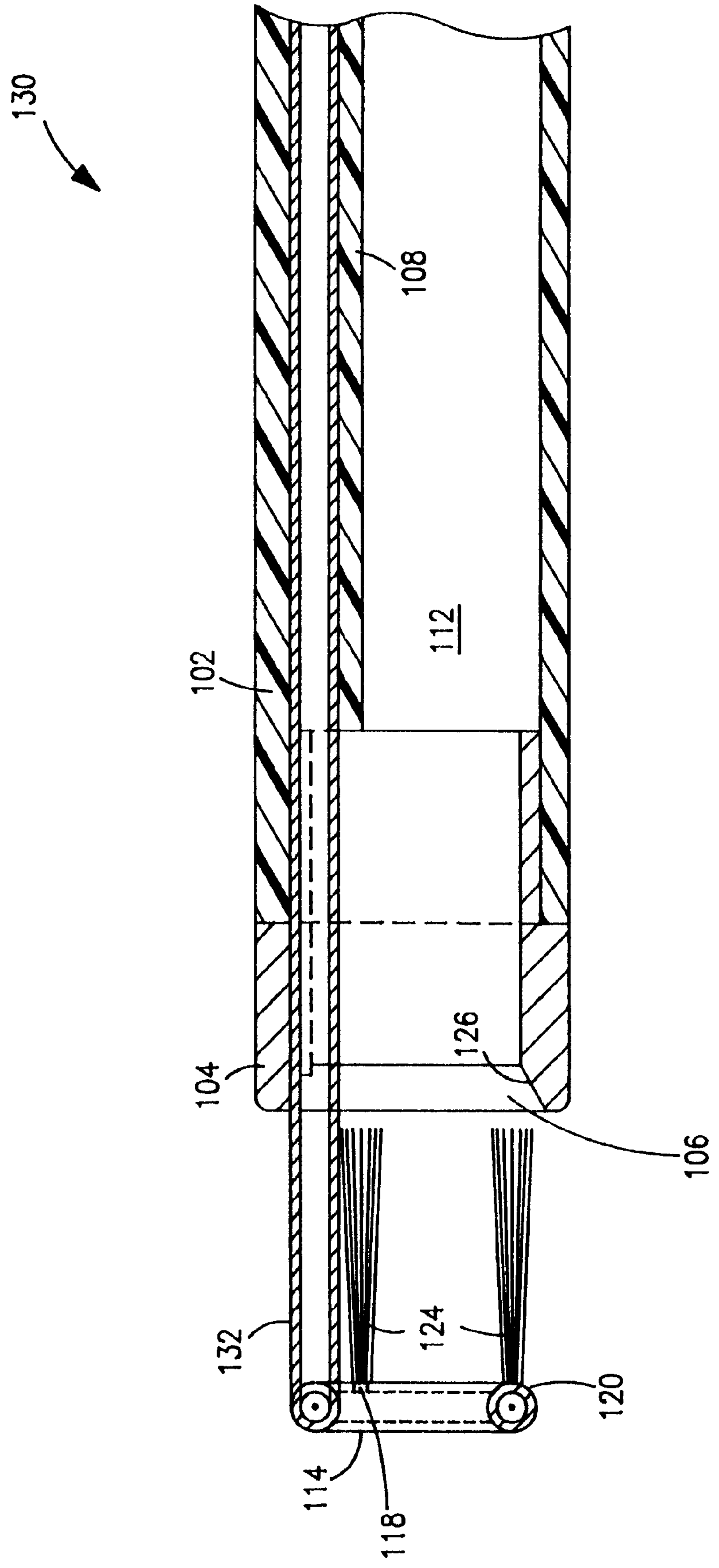
FIG. 8, an alternative embodiment, illustrates a cross-sectional view of another catheter distal end.

FIG. 8 illustrates a cross-sectional view of a catheter distal end 130 having like and similar component members to the catheter distal end 16 of FIG. 3 with the exception that the hypo tube now labeled 132 extends a greater distance past the tip member 104. All other numerals correspond to those elements previously described.

If the distance from the orifices 116, 118 and 120 to the opening 106 of the evacuation lumen 112 is large, such as greater than 5 mm, the catheter will loose much of the stagnation pressure formed from the impingement. of the fluid jets 124 on the opening to the evacuation lumen 112. Suction may be applied to the proximal end of the evacuation lumen to provide for removal of fragmented tissue. The device, however, will still entrain thrombus or tissue deposit into the localized low pressure region of the fluid jets 124 as long as the pressure at the distal end of the high pressure tubing is at least 500 psi.

FIG. 9 illustrates a cross-sectional view of an alternative embodiment of a catheter distal end 200 that is similar to that illustrated in FIG. 3 except that this catheter distal end 200 has been modified to provide for fluid jets with a component directed radially outwardly and of a lower energy than the proximally shooting fluid jets which impinge on the opening of the evacuation lumen. The distal end 200 is comprised of an outer plastic sheath 202, a manifolded tip 204 having an inner manifolded tip member 206 and an outer tip member 208 aligned over and about the inner manifolded tip member 206, a large external orifice 210, a septum 212 encompassing a hypo tube 214 and holding it to the inner surface of the outer plastic sheath 202, and an effluent evacuation lumen 216 incorporating the large external orifice 210 and further formed by the inner surface of the outer plastic sheath 202 and the septum 212. A loop 218 is located at the distal end of the hypo tube 214. The loop 218 allows the catheter to follow easily over a guidewire, but the distal end of the hypo tube is not required to be looped. Orifices 220, 222 and 224 (see FIG. 10) serve to direct jets 234 of fluid (e.g., saline) into the large external orifice 210 which communicates with effluent evacuation lumen 216.

The manifolded tip 204 of the distal catheter end 200, which has been modified to include both an inner manifolded tip member 206 and an outer tip member 208, provides a three stage manifolded tip 204 for reducing the pressure delivered to three radially outwardly directed orifices 226, 228 and 230 illustrated in FIG. 13 which serve to produce vadially outwardly directed or outwardly facing fluid jets 250, 251 and 252. This reduction in pressure provides for a lower velocity for these fluid jets and, consequently, these radially outwardly directed fluid jets 250, 251, and 252 are less traumatic than the rearwardly shooting fluid jets 234. The radially outwardly directed fluid jets 250, 251 and 252 help to clean thrombus or tissue deposit from the walls of blood vessels or tubules and bring the deposit into the rearwardly directed fluid jets 234 for fragmentation and removal.

The saline or high pressure liquid enters the proximal end of the high pressure hypo tube 214 and flows to the distal end of the high pressure hypo tube 214. Some of the liquid flows out of an opening 232 in the high pressure tube 214 into the first manifold space 236 and successive spaces 238 and 240 of the manifolded tip 204, and some liquid flows out of the orifices 220, 222 and 224 which direct the fluid jets 234 backwards toward the external orifice opening 210 to the effluent evacuation lumen 216. The fluid which enters the manifolded tip 204 still may possess significant localized kinetic energy which requires dissipation. As shown in this figure, the liquid is directed from the opening 232 and thence through the three stages of the manifolded tip 204 (i.e., three manifold spaces 236, 238 and 240 with flow resistance narrowings 242, 244, 246 and 248 between them as illustrated in FIGS. 11 and 12). The liquid is then expelled radially through the three exit side orifices 226, 228 and 230 of FIG. 13 with low velocity. Various manifold arrangements could be used to dissipate the kinetic and potential energy of the liquid prior to expelling the stream out of the catheter distal end.

FIG. 10 illustrates a cross-sectional view along line 10—10 of FIG. 9, where all numerals correspond to those elements previously described.

FIG. 11 illustrates a cross-sectional view along line 11—11 of FIG. 9 showing a flow resistance narrowing 242 leading from the manifold space 236 to the manifold space 238 of FIG. 12. All other numerals correspond to those elements previously described.

FIG. 12 illustrates a cross-sectional view along line 12—12 of FIG. 9 showing flow resistance narrowings 244, 246 and 248 between the manifold space 238 and the manifold space 240 of FIG. 13. All other numerals correspond to those elements previously described.

FIG. 13 illustrates a cross-sectional view along line 13—13 of FIG. 9 showing the manifold space 240 and the radially outwardly directed orifices 226, 228 and 230 in the walls of the outer tip member 208. All other numerals correspond to those elements previously described.

PIG. 14 illustrates a cross-sectional view of a catheter distal end 300 similar to that illustrated in FIG. 9 except that a balloon 219 has been added to the outer plastic sheath 202 proximal to the orifices 220, 222 and 224. The addition of a balloon is accomplished on this or any other catheter end so identified to contain a lumen which can carry a fluid (either gas or liquid) from the proximal end of the catheter to a more distal location in approximation with a balloon. The outer plastic sheath 202 is constructed of a dual lumen plastic construction where the balloon inflation lumen 213 (see FIG. 15) is the portion between the inner surface of the septum 212 and the outer plastic sheath 202. The high pressure hypo tubing 214 aligns in and utilizes the same balloon inflation lumen 213 for efficiency. The balloon 219 secures by adhesives 217 over and about the outer plastic sheath 202 and is inflated through an inflation port 215 connected to the balloon inflation lumen 213 (see FIG. 15). All other numerals correspond to those elements previously described.

FIG. 15 illustrates a cross-sectional view along line 15—15 of FIG. 14, where all numerals correspond to those elements previously described. Illustrated in particular is the balloon inflation lumen 213 and the balloon inflation port 215.

FIG. 16 illustrates a cross-sectional view of a catheter distal end 400 having a high pressure hypo tube 402 such as a metal hypo tube, polyimide tube or other high pressure tube which provides a pathway for saline or other high pressure liquid from the proximal end to the distal end of the catheter. The saline exits through one or more orifices 404, 406 or 408 (see FIG. 17) in the loop 410 and the high velocity jet streams 412 produced ar orifices 404, 406 and 408 impinge upon the impingement surface 414 of a target body 416. The high velocity of the jet streams 412 provides a localized low pressure which serves to draw thrombus or other tissue deposits into the jet streams 412 where it is fragmented into small pieces which will continue to get smaller as they are reintroduced into the high velocity jet streams 412. The impingement surface 414 provides a safety aspect to the catheter by prohibiting the jet streams 412 from coming into juxtaposition with the vessel cavity wall and causing unwanted trauma to healthy tissues. The target body 416 can be made as shown with a lumen 418 to allow for this catheter to pass over a standard guidewire in order to reach the lesion site in the blood vessel, tubule, or body cavity. The device can consist of only one high velocity jet stream with the impingement surface made smaller in surface area, or it can have up to ten jet streams. The preferred number of jet streams is three in order to clean thrombus around all sides of the vessel or tubule when a guidewire is in place. The device can be made without a guidewire lumen if desired. This device operates with a pressure in the distal end of the high pressure tube of at least 500 psi and preferably 1000–2000 psi. The high tube pressure is necessary to generate the large localized negative pressure at the jet streams required to provide for entrainment of thrombus or tissue deposit into the jet streams. A plastic protective covering 420 may be used to provide resistance to vessel trauma and aligns over and about the hypo tube 402.

FIG. 17 illustrates an end view of the catheter distal end 400 where all numerals correspond to those elements previously described.

Various modifications can be made to the present invention without departing from the apparent scope hereof.

FIG. 1 illustrates a representative example of various components of the catheter in device for tissue removal according to the present invention. Particular embodiments of the present invention may not require all elements shown in FIG. 1. For example, the catheters shown in FIGS. 3, 8, 9 and 16 do not contain a balloon and do not require inflation tube 48 and inflation fluid means 52. Similarly, the catheter shown in FIG. 16 does not provide for removal of debris and does not require effluent tubing 28, peristaltic pump 42, or tissue fragment collection reservoir 44.

THROMBECTOMY AND TISSUE REMOVAL METHOD AND DEVICE

PARTS

10 thrombectomy and tissue removal device
12 two-lumen catheter or two-passage tubular member
14 balloon
16 catheter distal end
18 guidewire
20 manifold
22 seal assembly
23 seal assembly
24 secondary branch
26 distal end
28 effluent tubing
30 seal assembly
32 roller
34 roller
36 roller
38 rotor
40 arrows
42 roller (peristaltic) pump
44 collection reservoir
46 secondary branch
48 inflation tube
50 seal assembly
52 inflation fluid means
54 sterile fluid container
56 high pressure supply means
58 tubing and coupling assembly
59 pump
60 high pressure fluid tube
62 secondary branch
64 lumen
66 compressible seal
68 surface
70 threaded knob
72 threads
74 point
76 lumen
78 lumen
80 point
82 lumen
84 metallic tubing or hypo tube
86 point
88 plastic tubing
89 point
90 point
91 point
92 point
93 point
94 point
95 point
102 plastic sheath
104 tip
106 external orifice
108 septum
1210 hypo tube
112 exhaust lumen or evacuation lumen
114 loop
116 orifice
118 orifice
120 orifice
124 fluid jet
126 beveled surface
130 catheter distal end
132 hypo tube
200 catheter distal end
202 outer plastic sheath
204 manifolded tip
206 inner manifold tip member
208 outer tip member
210 external orifice
212 septum
213 balloon inflation lumen
214 hypo tube
215 inflation port
216 effluent evacuation lumen
217 adhesive
218 loop
219 balloon
220 orifice
222 orifice
224 orifice
226 radially outwardly directed orifice
228 radially outwardly directed orifice
330 radially outwardly directed orifice
232 opening
234 fluid jet
236 manifold space
238 manifold space
240 manifold space
242 flow resistance narrowing
244 flow resistance narrowing
246 flow resistance narrowing
248 flow resistance narrowing
250 radially outwardly directed fluid jet
251 radially outwardly directed fluid jet
252 radially outwardly directed fluid jet
300 catheter distal end
400 catheter distal end
402 hypo tube
404 orifice
406 orifice
408 orifice
410 loop
412 high velocity jet stream
414 impingement surface

416 target body

418 lumen

420 plastic covering

We claim:

1. A device for removing thrombus or other tissue from an occluded or obstructed biological or synthetic body vessel or from a body cavity comprising:

a. a tubular member having a proximal end and a distal end, having a first passage and a second passage and a third passage extending along the length thereof, each passage with a proximal and distal end;

b. a high pressure fluid source sealingly attached to said proximal end of said first passage which drives a flow of high pressure fluid into said proximal end of said first passage;

c. said first passage comprising tubular means which carries the flow of high pressure fluid from said proximal end to said distal end, said distal end of said first passage having two or more orifices;

d. said second passage comprising tubular means for carrying a flow of fluid and emulsified tissue from said distal end to said proximal end, said distal end of said second passage being open;

e. fluid jets emanating from said orifices formed from the flow of of high pressure fluid carried by said first passage;

f. said third passage comprising tubular means for providing communication between said proximal and distal ends of said tubular member;

g. at least one of the fluid jets emanating from said distal end of said first passage impinges on said open distal end of said second passage ("impinging jets"), thereby providing stagnation pressure to drive the flow of emulsified tissue from said distal end of said second passage towards said proximal end of said second passage;

h. at least one of the fluid jets are "outwardly-facing jets" directed substantially away from said tubular member rather than being directed to impinge on said open distal end of said second passage of said tubular member; and, i. said proximal end of said second passage provides removal of the emulsified tissue from the body vessel or body cavity.

2. A device for removing thrombus or other tissue from an occluded or obstructed biological or synthetic body vessel or from a body cavity comprising:

a. a tubular member having a proximal end and a distal end, having a first passage and a second passage and a third passage extending along the length thereof, each passage with a proximal and distal end;

b. a high pressure fluid source sealingly attached to said proximal end of said first passage which drives a flow of high pressure fluid into said proximal end of said first passage;

c. said first passage comprising tubular means which carries the flow of high pressure fluid from said proximal end to said distal end, said distal end of said first passage having two or more orifices;

d. said second passage comprising tubular means for carrying a flow of fluid and emulsified tissue from said distal end to said proximal end, the distal end of said second passage being open;

e. fluid jets emanating from said orifices formed from the flow of high pressure fluid carried by said first passage;

f. said third passage comprising tubular means for providing communication between said proximal and distal ends of the tubular member;

g. at least one of the fluid jets emanating from said distal end of said first passage impinges on said open distal end of said second passage ("impinging jets"), the said high pressure fluid in the said first passage being under high pressure greater than approximately 500 psi, providing sufficient energy in the jets to cut or emulsify harder tissue;

h. at least one of the fluid jets are "outwardly-facing jets" directed substantially away from said tubular member rather than being directed to impinge on said open distal end of said second passage of said tubular member; and, i. said proximal end of said second passage provides removal of the emulsified tissue from the body vessel or body cavity.

3. The device of claim 1 or 2 wherein the outwardly-facing jet(s) have lower fluid velocity than the impinging jets.

4. The device of claim 3 further comprising a fluid resistance narrowing found in said distal end of said first passage which by virtue of narrowed region(s) creates pressure losses and thereby provides for said lower fluid velocity of said outwardly-facing jet(s).

5. The device of claim 3 as wherein any or a combination of fluid resistance narrowing(s) dissipate and distribute energy and provide for the lower fluid velocity.

6. A device for removing thrombus or other tissue from an occluded or obstructed biological or synthetic body vessel or from a body cavity comprising;

a. a tubular member having a proximal end and a distal end, having a first passage and a second passage and a third passage extending along the length thereof, each passage with a proximal and distal end;

b. a high pressure fluid source sealinqly attached to said proximal end of said first passage which drives a flow of high pressure fluid into said proximal end of said first passage;

c. said first passage comprising tubular means which carries the flow of high pressure fluid from said proximal end to said distal end, said distal end of said first passage having two or more orifices;

d. said second passage comprising tubular means for carrying a flow of fluid and emulsified tissue from said distal end to said proximal end, said distal end of said second passage being open;

e. fluid jets emanating from said orifices formed from the flow of of high pressure fluid carried by said first passage;

f. said third passage comprising tubular means for providing communication between said proximal and distal ends of said tubular member;

g. at least one of the fluid jets emanating from said distal end of said first passage impinges on said open distal end of said second passage ("impinging jets"), thereby providing a low pressure region which tends to bring the tissue towards the jet(s);

h. at least one of the fluid jets are "outwardly-facing jets" directed substantially away from said tubular member; and, i. said proximal end of said second passage provides removal of the emulsified tissue from the body vessel or body cavity.

7. The device of claim 1, 6 or 2 further comprising a metering means which is connected to said proximal end of said second passage to control the flow of fluid and emulsified tissue in said second passage at a controlled rate of flow less than the rate of flow which would result without said metering means.

8. The device of claim 7 wherein said metering means consists of a roller pump.

9. The device of claim 7 wherein said metering means controls the rate of flow of fluid and emulsified tissue in said second passage at a rate of flow controlled relative to the rate of flow of high pressure fluid in the first passage.

10. The device of claim 1, 6 or 2 further comprising a suction means which is connected to said proximal end of said second passage to control the flow of fluid and emulsified tissue in said second passage at a controlled rate of flow greater than the rate of flow which would result without said suction means.

11. The device of claim 10 wherein said suction means consists of a roller pump.

12. The device of claim 10 wherein said suction means controls the rate of flow of fluid and emulsified tissue in said second passage at a rate of flow controlled relative to the rate of flow of high pressure fluid in the first passage.

13. The device of claim 1, 6 or 2 wherein said high pressure fluid source is a positive-displacement piston pump.

14. The device of claim 1, 6 or 2 wherein therapeutic material is delivered through said first passage of said tubular member.

15. The device of claim 14 wherein the high pressure fluid carried in said first passage contains the therapeutic material; thereby the fluid jets emanating from said distal portion of said first passage also contain the therapeutic material.

16. The device of claim 1, 6 or 2 wherein diagnostic medium is delivered through said second passage of said tubular member.

17. The device of claim 16 wherein the high pressure fluid carried in said first passage contains the diagnostic medium; thereby the fluid jets emanating from said distal portion of said first passage also contain the diagnostic medium.

18. The device of claim 1, 6 or 2 wherein said second passage of said tubular member also provides passage for a catheter device.

19. The device of claim 1, 6 or 2 wherein said third passage provides communication between said proximal and distal ends of said tubular member for, passage of a guidewire device.

20. The device of claim 1, 6 or 2 wherein said distal end of said first passage is formed into an arcuate shape extending beyond said second passage to direct one or more of the jets onto said distal end of said second passage.

21. The device of claim 20 wherein the fluid jets emanate from various points along said arcuate-shaped portion of said first passage; when a guidewire device is in position near said distal end of said first passage and extends through said arcuate-shaped first passage, the jets are therefore oriented at various points around the guidewire device thereby decreasing any effect that the guidewire device may have in shielding the tissue from the effects of the jets.

22. The device of claim 1, 6 or 2 wherein said distal end of said first passage is formed into a toroidal shape which is oriented in a plane perpendicular to the axis of said tubular member and distal to said distal end of said second passage.

23. The device of claim 22 wherein the fluid jets emanate from various points along the toroidal-shaped portion of said first passage; when a guidewire device is in position through said distal end of said second passage and extends further through said toroidal-shaped portion of said first passage. the jets are therefore oriented at various points circumferentially around the guidewire device thereby decreasing any effect that the guidewire device may have in shielding the tissue from the effects of the jets.

* * * * *